United States Patent [19]

Brewer

[11] Patent Number: 4,959,199

[45] Date of Patent: Sep. 25, 1990

[54] AUTOCLAVABLE MODULAR CASSETTE AND TRAY FOR HOLDING DENTAL INSTRUMENTS

[76] Inventor: Charles A. Brewer, 105 Via Wazier, Newport Beach, Calif. 92660

[21] Appl. No.: 157,879

[22] Filed: Feb. 19, 1988

[51] Int. Cl.[5] .................. A61L 2/20; B65D 45/16; B65D 51/16

[52] U.S. Cl. .................. 422/300; 422/292; 422/297; 422/310; 206/439; 206/63.5

[58] Field of Search .............. 422/292, 297, 300, 310; 206/439, 63.5

[56] References Cited

U.S. PATENT DOCUMENTS

| | | | |
|---|---|---|---|
| 4,541,992 | 9/1985 | Jerge et al. | 422/300 |
| 4,643,303 | 2/1987 | Arp et al. | 422/300 X |
| 4,762,688 | 8/1988 | Berry, Jr. | 422/300 X |
| 4,774,063 | 9/1988 | Runnels | 422/300 X |
| 4,798,292 | 1/1989 | Hauze | 206/439 |

Primary Examiner—Robert J. Warden
Assistant Examiner—Jill Johnston
Attorney, Agent, or Firm—Klein & Szekeres

[57] ABSTRACT

A cassette for dental instruments includes two substantially identical trays with each tray having a hinge to permit removable assembly of the tray to the other tray to form the cassette or enclosure. Each tray has apertures or holes wherethrough liquid cleansing agents can be sprayed into and can be drained out of the tray. Ribs are removably mounted into the trays and are held in spaced substantially parallel positions therein. At least one of the ribs has a clamping device for holding dental instruments in positions substantially transverse to the ribs. An intermediate locking plate is removably mounted into each tray above the ribs to further secure the dental instruments in their clamped positions in the tray. The two trays when assembled together as a cassette are readily washed, autoclaved, stored and transported together, while each tray can contain a separate set of dental instruments.

20 Claims, 4 Drawing Sheets

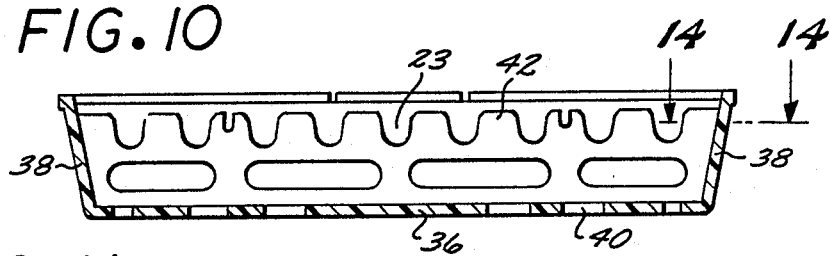
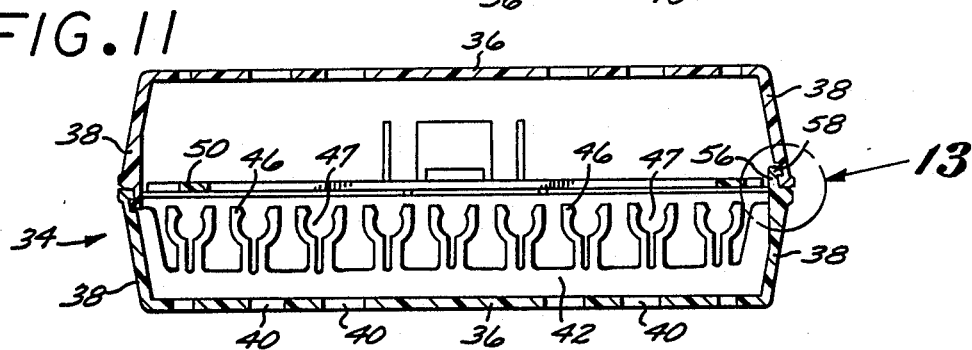
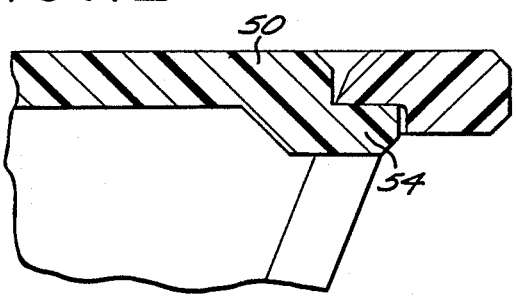
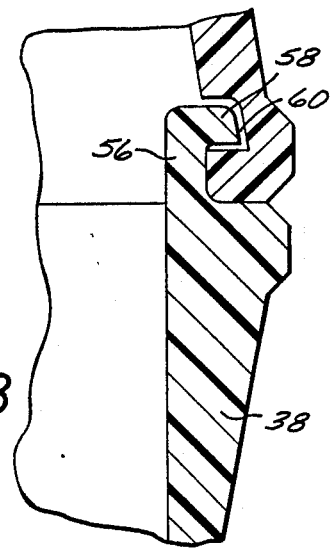
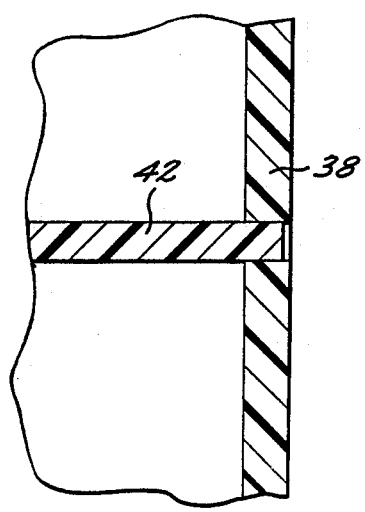
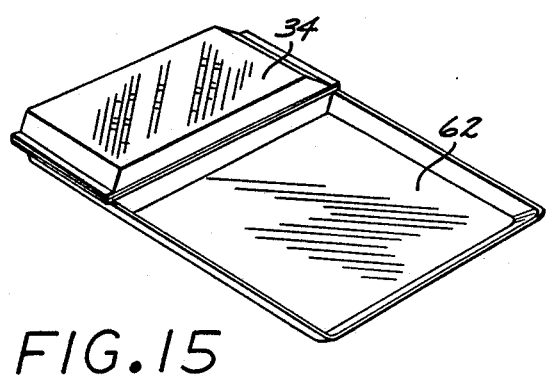

AUTOCLAVABLE MODULAR CASSETTE AND TRAY FOR HOLDING DENTAL INSTRUMENTS

FIELD OF THE INVENTION

The present invention is directed trays or cassettes for holding dental instruments. More particularly, the present invention is directed to a modular cassette in which two sets of dental instrument may be sterilized, stored, transported and held ready for use by a dentist or dental hygienist.

BRIEF DESCRIPTION OF THE PRIOR ART

Trays or cassettes for dental instruments are known in the prior art. More particularly, a prior art cassette for dental instruments is shown on FIG. 1 of the drawings appended to the present application for U.S. Pat. No. Such a prior art tray comprises a lower tray member 20, having a plurality of transverse supports 21, and an upper cover member 22 which is hingedly and removably connected to the tray member 20. The transverse supports 21 have substantially round indentations or openings 23 into which elongated dental instruments, such as dental mirrors 24 and tartar scrapers 25 (shown on FIG. 3 of the present application) and like conventional dental instruments may be placed.

When the dental instruments are not used, the lid or upper cover member 22 of the cassette is usually closed. Holes or apertures 26 in the lower tray 20 and in the lid 22 usually allow cleaning of the dental instruments by spraying detergent and disinfectant solutions into the cassette and permitting subsequent drainage of the liquids from the cassette. The cleaning process may also be aided by application of ultrasound, and sterilization is accomplished by autoclaving the cassette containing the instruments.

Although the above described and similar cassettes for holding dental instruments function adequately, recent trend in the field has demonstrated a need for greater efficiency, in terms of less manual handling of tools and instruments, and also a need for significantly lesser chance for health care personnel to be accidentally wounded by used dental instruments. In other words, there is currently a need in the field for dental cassettes and trays which minimize further the amount of manual handling and washing required in connection with every day use of dental instruments. Moreover, and particularly because of the current acquired immunodefiency syndrome (AIDS) epidemic, there is a strong need in the field for such handling of used dental instruments which virtually eliminates accidental cutting or wounding of a health care worker (dentist, dental hygienist or assistant) with used, and possibly AIDS contaminated dental instruments. The modular cassette of the present invention meets this need.

SUMMARY OF THE INVENTION

It is an object of the present invention to provide a modular cassette for dental instruments which comprises two substantially identical trays, each of which is capable of holding a separate set of dental instruments.

It is another object of the present invention to provide a modular cassette for dental instruments which meets the foregoing objects, and which minimizes exposure of health care workers to accidental woundings by used dental instruments.

It is still another object of the present invention to provide a modular cassette for dental instruments which meets the foregoing objects and which permits easy separation and assembly of the two trays of the cassette to one another, by only one hand of the health care worker.

It is yet another object of the present invention to provide a modular cassette for dental instruments which meets the foregoing objects and which permits washing and sterilization of the cassette and of the instruments contained therein, without removing the instruments from the cassette.

The foregoing and other objects and advantages are attained by a cassette for the dental instruments which includes two substantially identical trays with each tray having a hinge to permit removable assembly of the tray to the other tray to form the cassette or enclosure. Each tray has a plurality of apertures or holes wherethrough liquid cleansing agents can be sprayed into and can be drained out of the tray.

A plurality of ribs are removably mounted into the trays to occupy spaced, substantially parallel positions therein. At least one of the ribs includes clamping means for holding a plurality of dental instruments in positions substantially transverse to the ribs. An intermediate locking plate is removably mounted into each tray above the ribs to further secure the dental instruments in their clamped in positions in the tray.

The two trays are readily washed, autoclaved, stored and transported as a cassette, containing two separate sets of dental instruments. The two trays of one cassette are also readily separated from one another to enable one or more health care workers to work with the two separate sets of instruments.

The features of the present invention can be best understood, together with further objects and advantages, by reference to the following description taken in connection with the accompanying drawings.

BRIEF DESCRIPTION OF THE DRAWINGS

FIG. 10 is a cross-sectional view taken on lines 10,10 of FIG. 2;

FIG. 11 is another cross-sectional view of the assembled cassette of the preferred embodiment;

FIG. 12 is an enlarged view of the area indicated on FIG. 4;

FIG. 13 is an enlarged view of the area indicated on FIG. 11;

FIG. 14 is a cross-sectional view taken on lines 14,14 of FIG. 10; and

FIG. 15 is a perspective view showing the preferred embodiment on a B sized dental tray.

DESCRIPTION OF THE PREFERRED EMBODIMENTS

The following specification taken in conjunction with the drawings sets forth the preferred embodiment of the present invention. The embodiments of the invention disclosed herein are the best modes contemplated by the inventor for carrying out his invention in a commercial environment, although it should be understood that various modifications can be accomplished within the parameters of the present invention.

Figure 1:
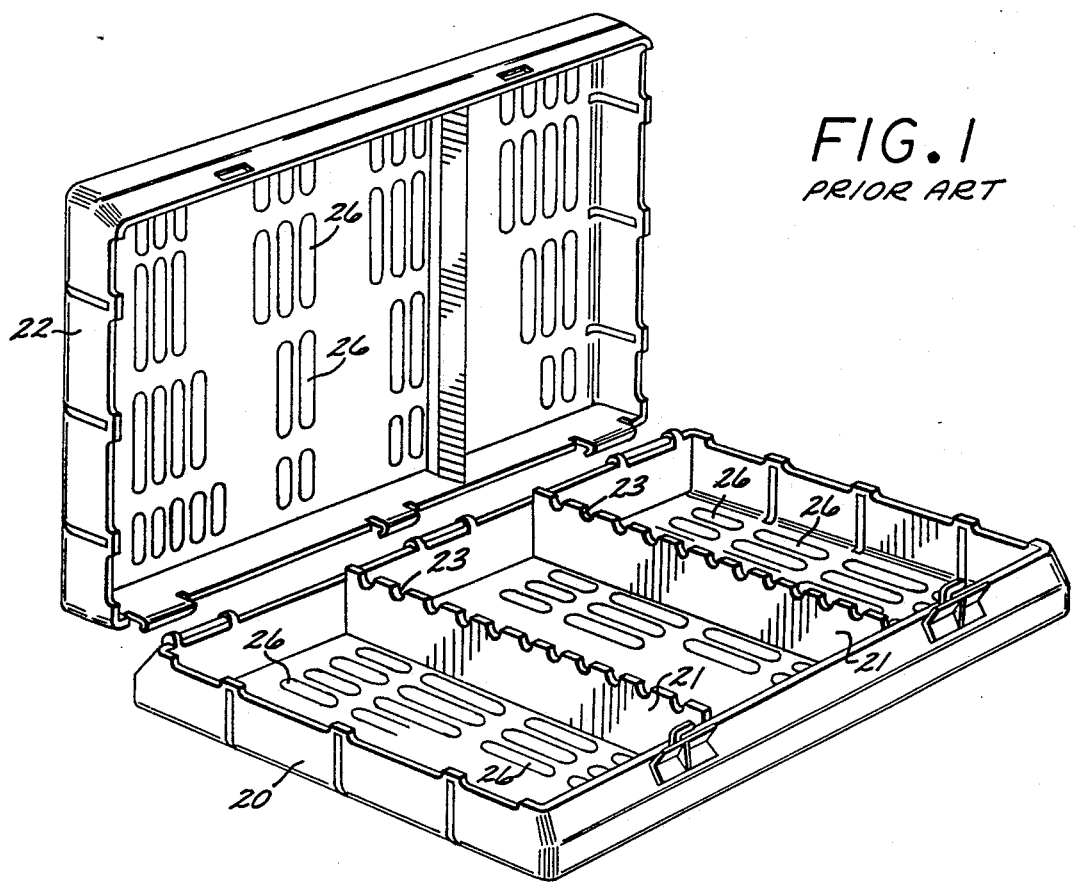
FIG. 1 is a partially exploded perspective view of a dental instrument cassette of the prior art.
Figure 2:
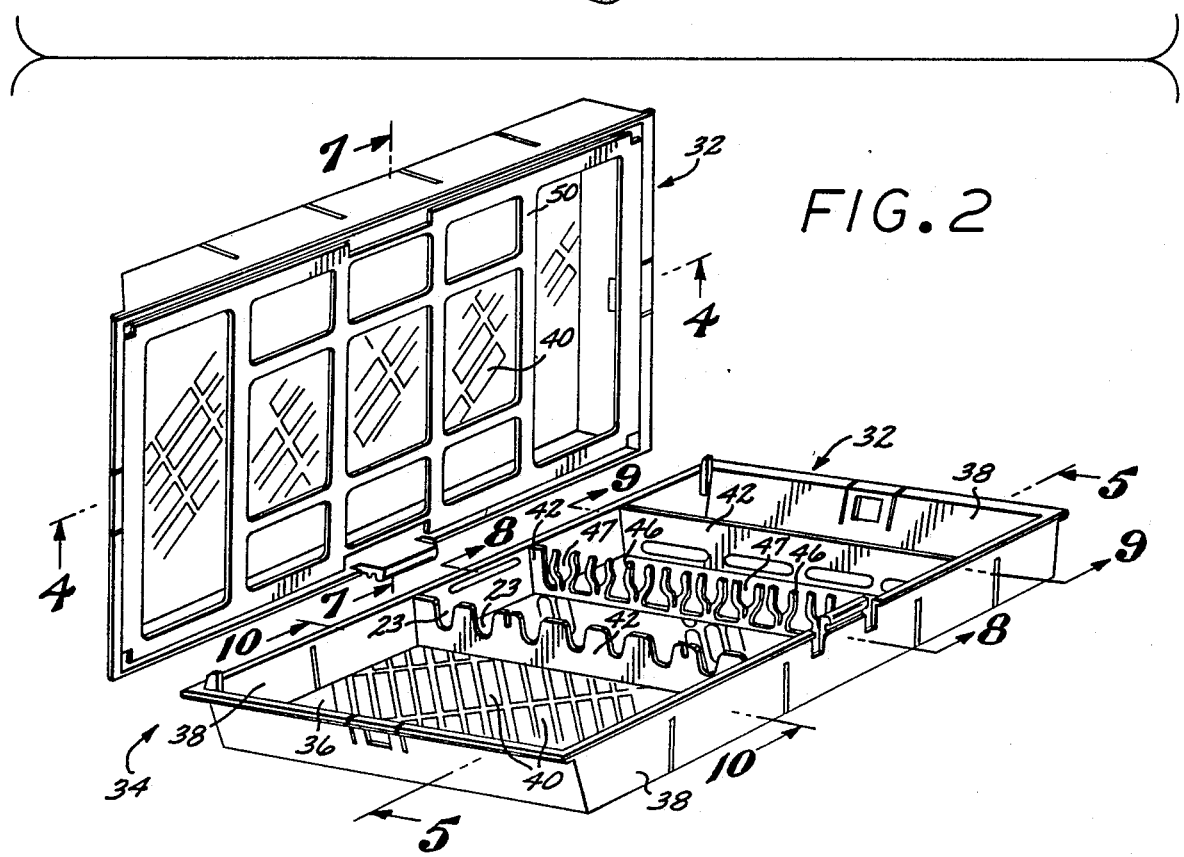
FIG. 2 is a partially exploded perspective view of a preferred embodiment of the cassette of the present invention, one intermediate locking plate being omitted from the view.
Figure 3:
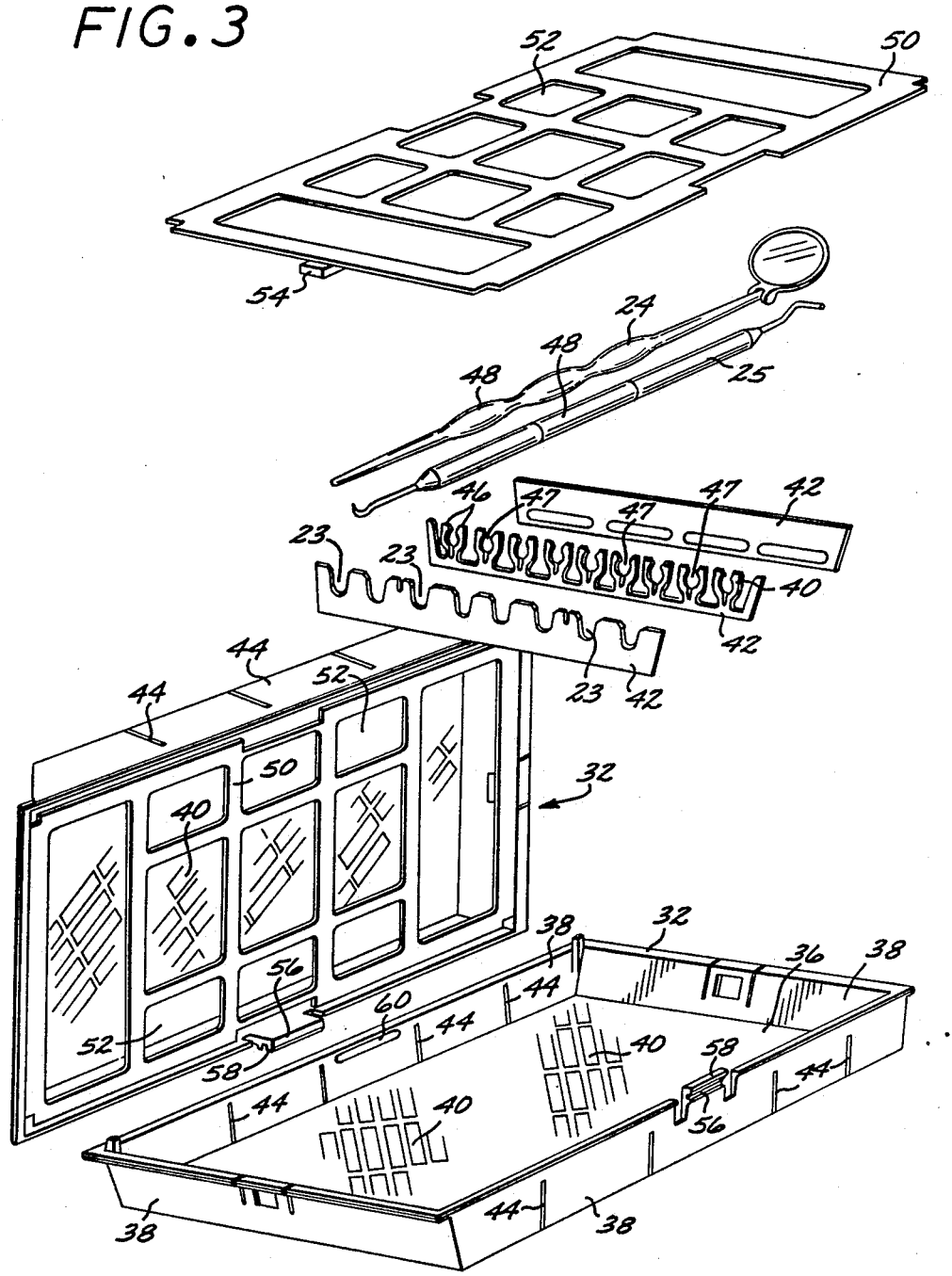
FIG. 3 is another partially exploded perspective view of the preferred embodiment.

Referring now to the drawing Figures, and particularly to the perspective view of FIGS. 2 and 3, the preferred embodiment of the modular cassette - dental tray of the present invention is disclosed.

Figure 6:
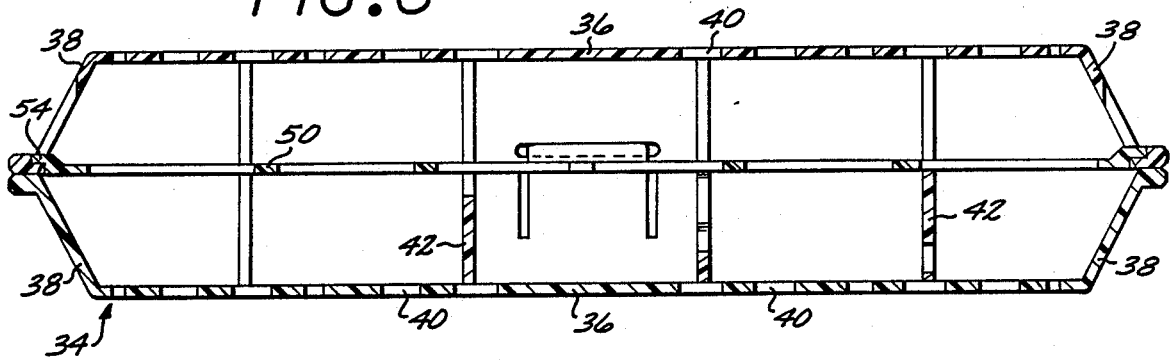
FIG. 6 is a cross-sectional view of the assembled cassette formed by the preferred embodiment.
Figure 7:
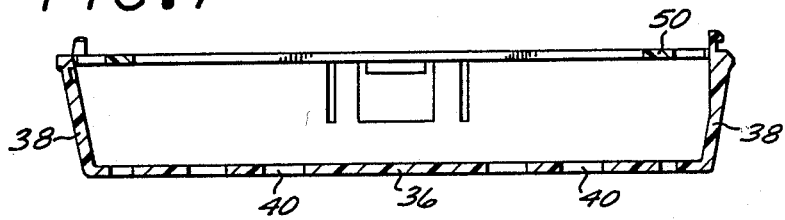
FIG. 7 is a cross-sectional view taken on lines 7,7 of FIG. 2.
Figure 8:
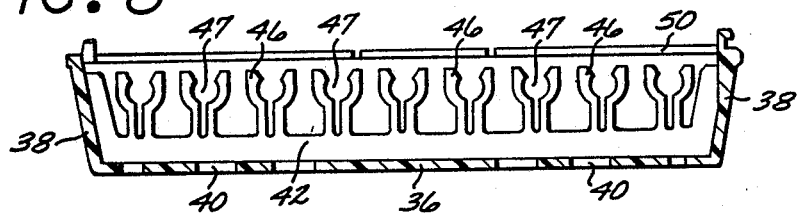
FIG. 8 is a cross-sectional view taken on lines 8,8 of FIG. 2.
Figure 9:
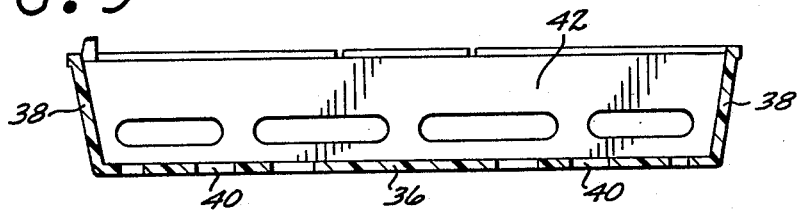
FIG. 9 is a cross-sectional view taken on lines 9, 9 of FIG. 2.

The modular cassette-dental tray of the invention comprises two substantially identical trays 32, which can be assembled to one another to form an enclosure or cassette 34. The enclosure or cassette 34 is shown in closed positions i.e. in positions where the trays 32 are fully assembled to one another on the cross-sectional views of FIGS. 6 and 11.

Each tray 32 of the herein described preferred embodiment has a substantially flat main plate 36 and four side walls 38 which are attached to the periphery of the main plate 36 at oblique angles relative to the main plate 36. The main plate 36 has a plurality of substantially evenly spaced, rectangular, relatively large apertures or openings 40 disposed obliquely relative to the longitudinal axis of the tray 32. It should be apparent from the foregoing and from an inspection of the drawing Figures that that the large apertures 40 render the cassette 34 of the assembled trays 32 permeable to fluids, and therefore permit washing of the cassette 34 and its contents with liquids, drying it with air, and sterilization by autoclaving at the usual autoclaving temperatures of approximately 250° to 300° F.

A plurality of ribs 42 are removably mounted into each tray 32 in positions wherein the ribs 42 are substantially transverse to the longitudinal axis of the tray 32, and the ribs 42 are substantially evenly spaced relative to one another. In the herein described preferred embodiment evenly spaced, aligned slots 44 are provided in the two longer, opposite side walls 38 of the tray 32. The slots 44 are well shown on FIG. 3. Advantageously, the ribs 42 are mounted into the slots 44 by inserting them into the slots 44. This is shown in the detailed, enlarged view of FIG. 14. In alternative embodiments (not shown) other means for mounting the ribs 42 to the tray 32 may be provided. The structure described above, and shown in the appended Figures, particularly on FIG. 3, also permits a user (not shown) to rearrange the positioning of the ribs 42 in the tray 32. Preferably, as is shown in the drawings, three ribs 42 are mounted in a tray 32 having slots 44 for accomodating four ribs 42.

It is an important novel feature of the present invention that at least one of the ribs 42 mounted into at least one tray 32 of the cassette of the invention includes clamping or holding means for capturing and removably holding elongated dental instruments, such as the dental mirror 24, and tartar scraper 25, (shown on FIG. 3) in the tray 32. As is shown in the attached figures, the clamping means or holding means preferably are integrally constructed with the rib 42. In the herein described preferred embodiment they comprise several pairs of upwardly extending posts 46 which form Y configurations. The elongated handles 48 of dental instruments are slightly larger in diameter than a narrow restriction 47 in the Y configuration, so that the handle 48 "snaps into" and is removably captured in the Y configuration below the restriction 47.

In addition to the rib 42 having the holding means, at least one other rib 42 is provided as an additional feature of the present invention. The additional rib 42 has support means for supporting the dental instruments in the positions wherein they are held by the holding means. In the herein described preferred embodiment the support means comprise a plurality of substantially round indentations 23 in the rib 42, which are configured to accommodate the handles 48 of the dental instruments.

Figure 4:
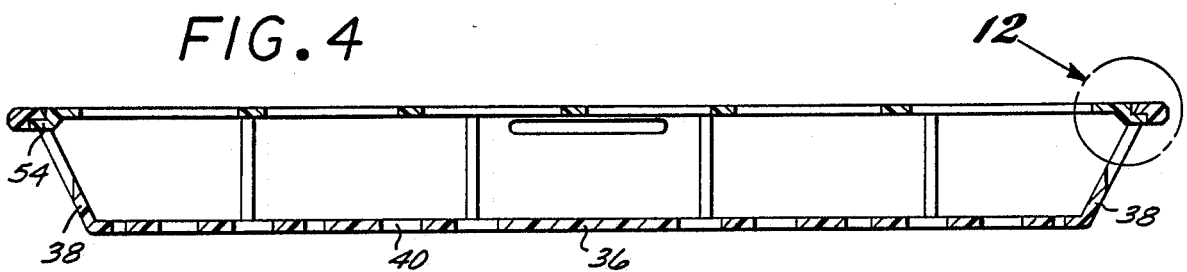
FIG. 4 is a cross-sectional view taken on lines 4,4 of FIG. 2.
Figure 5:
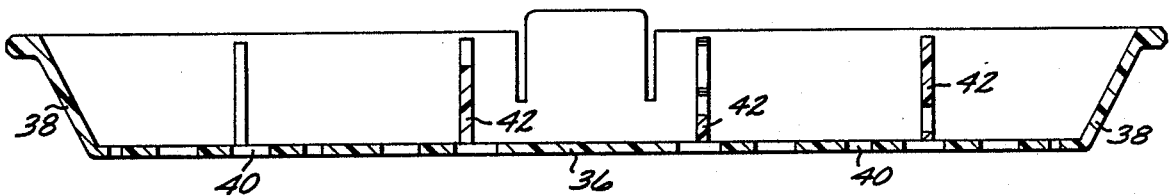
FIG. 5 is a cross-sectional view taken on lines 5,5 of FIG. 2.

As still another feature of the present invention, an intermediate locking plate 50 is disposed above the ribs 42 of each tray 32. The locking plate 50, like the main plate 36 of the trays 32, has a plurality of large apertures 52 so as to permit cleansing liquids and air to freely penetrate into the interior of the cassette 34. The intermediate locking plate 50 has forwardly and rearwardly extending tabs or tongues 54, only one of which is shown on FIG. 3. The tab 54 fits into a complementary opening in the side walls 38 of the tray 32. This is well shown in the cross-sectional views of FIGS. 4 and 12.

The two trays 32 of the cassette 34 are identical in construction, although they may have different kinds and different number of ribs 42 mounted in them. The two trays 32 are removably assembled to one another though a hinge mechanism which is described below with reference to FIGS. 2, 3, 11 and 13.

Each tray 32 has a hinge tab or tongue 56 protruding upwardly substantially in the center of one of the longer side walls 38 of the tray 32. The hinge tongue 56 has an outwardly protruding ear 58. The hinge tongue and ear 58 would also be appropriately called a snap tonge and ear, as the ear snaps into the herein below described openings. Thus an elongated indentation or opening 60 is located substantially in the center of the side wall 38, which is opposite to the side wall 38 having the hinge tongue 56 and ear 58. The opening 60 is complementary to the ear 58 so that the ear 58 fits into it, as shown on FIG. 13. When the two trays 32 are assembled to one another, the hinge tongue 56 and ear 58 of each tray 32 is applied to the complementary opening 60 of the other tray 32. The assembly and disassembly of the trays 32 to one another, can be readily accomplished with one hand (not shown.) For disassembly, a health care worker needs to press one of the hinge tongues 56 inwardly so as to disengage the ear 58 from the opening 60.

The entire cassette 34, including the ribs 42 and locking plates 50 is made from such plastic material which withstands sterilization by autoclaving at approximately 250° to 300° F. Suitable plastic materials are poly ether sulfone, poly sulfone and poly phenylene sulfide. The presently preferred material is poly ether sulfone, and the cassette 34 and component parts are readily made by injection molding.

The use and advantages of the above described modular cassette-dental instrument trays of the present invention are readily apparent to those skilled in the art from the foregoing disclosure. In summary, a separate set of clear sterilized dental instruments may be kept in each tray 32. The dental instruments are securely held in the trays 32 by the clamping means and by the locking plate 50. The two trays 32 are readily assembled to one another, using only one hand. The cassette 34, comprising the two trays 32 is dimensioned to fit transversely, and is therefore carried conveniently, on a B size dental tray 62, as is shown FIG. 15.

When desired, the cassette 34 is separated with one hand into two trays 32, to provide two separate sets of dental instruments. The locking plate 50 is also removed and reinserted readily with one hand. After use the dental instruments are replaced in the tray 32, the trays 32 are locked with the locking plate 50, and are finally reassembled to form the cassette 34. The cassette 34 with its contents is then cleansed and sterilized without the instruments being touched by human hands, to render the dental instruments useable again. The foregoing demonstrates that the modular cassette-dental instruments tray of the present invention minimizes human handling of dental instruments, and thereby minimizes dangerous exposure to accidental wounding of health care workers by used and potentially contaminated instruments.

Another feature and advantage of the present invention is that when the intermediate locking plates 50 are removed, the trays 32 readily stack on one another with the open face facing upward. This is clearly advantageous for storage.

Further advantages and modifications of the invention may become readily apparent to those skilled in the art in light of the foregoing disclosure. Therefore, the scope of the present invention should be interpreted solely from the following claims, as such claims are read in light of the disclosure.

What is claimed is:

1. An autoclavable cassette for holding dental instruments, comprising:
    two substantially identical trays, each tray having hinge means for removably assembling the tray to the other tray to form an enclosure, and a plurality of apertures wherethrough liquid can be sprayed into and can be drained out of the enclosure;
    a plurality of ribs mountable into each tray substantially parallel with one another, at least one of said ribs having clamping means for holding a plurality of elongated dental instruments in substantially transverse position to the ribs; and
    an intermediate locking plate removably mountable into each tray above the plurality of ribs, whereby a separate set of dental instruments can be placed into each tray, and whereby the trays assembled through the hinge means to form the enclosure, can be ultrasound cleaned and autoclaved.

2. The cassette for holding dental instruments of claim 1 wherein the hinge means comprise a hinge tongue protruding from each tray and a complementary opening to the tongue in each tray, the opening being configured to removably receive the hinge tongue.

3. The cassette for holding dental instruments of claim 1 wherein the intermediate locking plate has a pair of protruding tongues, the tongues being spaced and protruding outwardly on opposite sides of the locking plate, and wherein each tray comprises openings complementary to the protruding tongues and adapted for receiving the protruding tongues whereby the locking plate is removably mounted into the tray.

4. The cassette for holding dental instruments of claim 1 wherein each tray has at least a pair of oppositely disposed side walls, wherein the side walls have substantially regularly spaced aligned slots, and wherein the ribs are removably mounted into said aligned slots.

5. The cassette for holding dental instruments of claim 1 wherein the clamping means comprise a plurality of substantially evenly spaced pairs of posts attached to the rib each pair of posts substantially forming a Y configuration, and having a restriction to resiliently capture the dental instruments.

6. The cassette for holding dental instruments of claim 1 further comprising at least one rib having support means for supporting the plurality of dental instruments held by the clamping means in their positions substantially transverse to the ribs.

7. The cassette for holding dental instruments of claim 1 wherein each tray is substantially rectangular, and wherein each tray is dimensioned to fit transversely on a B sized dental tray.

8. The cassette for holding dental instruments of claim 1 wherein the cassette consists essentially of plastic material selected from the group consisting of poly ether sulfone, poly sulfone and poly phenylene sulfide.

9. The cassette for holding dental instruments of claim 1 wherein each tray has a main plate, and wherein the apertures are substantially evenly spaced in the main plate.

10. The cassette for holding dental instruments of claim 1 wherein each tray contains the parallel disposed evenly spaced ribs. of the ribs has a clamping device for holding dental instruments in positions substantially transverse to the ribs. An intermediate locking plate is removably mounted into each tray above the ribs to further secure the dental instruments in their clamped positions in the tray. The two trays when assembled together as a cassette are readily washed, autoclaved, stored and transported together, while each tray can contain a separate set of dental instruments.

11. An autoclavable modular cassette for holding dental instruments comprising:
    two substantially identical trays, the trays having hinge means for removably assembling the trays to one another, each tray having a main plate having a plurality of apertures wherethrough a liquid can be sprayed into and can be drained out of the tray, and at least a pair of parallel side walls, disposed on opposite edges of the main plates;
    a plurality of ribs which are mounted into each tray to occupy substantially parallel positions therein substantially transverse to the general longitudinal axis of the tray, and extending substantially from side wall to side wall, one of the trays including clamping means for holding a plurality of elongated dental instruments in positions substantially transverse to the ribs, the clamping means including
    substantially Y shaped posts protruding upwardly from one of the ribs;
    the trays and the ribs being made of autoclavable plastic material whereby a separate set of dental instruments can be placed into each tray, and whereby the assembled trays forming on the enclosure containing two sets of dental instruments can be cleaned with liquid and ultrasound and can be autoclaved.

12. An autoclavable modular cassette for holding dental instruments comprising:
    two substantially identical trays, the trays having hinge means for removably assembling the trays to one another, each tray having a main plate having a plurality of apertures wherethrough a liquid can be sprayed into and can be drained out of the tray, and at least a pair of parallel side walls, disposed on opposite edges of the main plates;

a plurality of ribs which are mounted into each tray to occupy substantially parallel positions therein substantially transverse to the general longitudinal axis of the tray, and extending substantially from side wall to side wall, one of the trays including clamping means for holding a plurality of elongated dental instruments in positions substantially transverse to the ribs;

two intermediate locking plates, each intermediate locking plate being removably mountable to one tray in position above the ribs, the trays and the ribs being made of autoclavable plastic material whereby a separate set of dental instruments can be placed into each tray, and whereby the assembled trays forming on the enclosure containing two sets of dental instruments can be cleaned with liquid and ultrasound and can be autoclaved.

13. The autoclavable modular cassette of claim 12 wherein the side walls of the trays have a plurality of substantially evenly spaced aligned slots, the ribs being removably mountable into said slots.

14. The autoclavable modular cassette of claim 12 wherein at least one of the ribs includes support means for supporting the plurality of elongated dental instruments in their transverse positions relative to the ribs.

15. The autoclavable modular cassette of claim 14 wherein the hinge means comprise a tongue protruding from one side wall of the tray and an opening in the opposite side wall of the tray, the opening being configured to removably receive the hinge tongue of the other tray.

16. The autoclavable modular cassette of claim 15 wherein each intermediate locking plate has a pair of prongs protruding outwardly, forward and rearward from the locking plate, and wherein each tray has complementary openings adapted for removably receiving the prongs.

17. The autoclavable modular cassette of claim 15 consisting essentially of plastic material selected from the group consisting of poly ether sulfone, poly sulfone and poly phenylene sulfide.

18. The autoclavable modular cassette of claim 15 consisting essentially of plastic material which is capable of withstanding autoclaving temperatures of approximately 250° F to 300° F.

19. An autoclavable modular cassette for holding dental instruments, comprising:

two substantially identical trays, each tray having a substantially rectangular main plate and four side plates attached substantially to the edges of the main plate;

a hinge tongue and ear perpendicular to the tongue protruding from a first side of the tray, and an opening in the opposite second side wall of the tray, the opening being configured to removably receive the hinge ear of the other tray, whereby the two trays can be removably mounted to one another;

a plurality of ribs mounted into each tray, at least one of said ribs comprising means for supporting the plurality of dental instruments in transverse positions relative to the ribs; and a pair of intermediate locking plates, each locking plate being removably mountable to one of the trays above the ribs, the locking plates having a plurality of apertures, and the main plates of the trays, having a plurality of apertures, the entire assembly of trays, ribs and locking plates being made of autoclavable plastic material capable of withstanding autoclaving temperatures of 250° to 300° F., whereby separate sets of dental instruments can be placed and contained in each tray, and the assembled trays, which form an enclosure can be washed with liquid, can be ultrasound cleaned and autoclaved while the two sets of dental instruments are contained therein.

20. The cassette for holding dental instruments of claim 19 consisting essentially of plastic materials selected from a group consisting of poly ether sulfone, poly sulfone and poly phenylene sulfide.

* * * * *